United States Patent

Zimmer et al.

Patent Number: 5,379,334
Date of Patent: Jan. 3, 1995

[54] OBJECT TESTING SYSTEM

[75] Inventors: Manfred Zimmer, Mainz; Rainer Henkel, Wiesbaden; Rainer Bermbach, Mainz, all of Germany

[73] Assignee: Heimann Systems GmbH & Co. KG, Wiesbaden, Germany

[21] Appl. No.: 116,607

[22] Filed: Sep. 7, 1993

Related U.S. Application Data

[63] Continuation of Ser. No. 94,387, Jul. 20, 1993.

[30] Foreign Application Priority Data

Jul. 20, 1992 [EP] European Pat. Off. ............ 92112381

[51] Int. Cl.⁶ .................................................. G01N 23/04
[52] U.S. Cl. ................................. 378/98.2; 378/98.7; 378/62
[58] Field of Search ................ 378/98.2, 98.7, 98.9, 378/57, 51, 62, 53

[56] References Cited

U.S. PATENT DOCUMENTS

| | | | |
|---|---|---|---|
| 4,149,082 | 4/1979 | Haendle et al. | 378/98.2 |
| 4,599,740 | 7/1986 | Cable | 378/57 |
| 4,987,584 | 1/1991 | Doenges | 378/98.7 |
| 5,077,769 | 12/1991 | Franciose | 378/98.2 |
| 5,260,982 | 11/1993 | Fujii et al. | 378/57 |

FOREIGN PATENT DOCUMENTS

| | | | |
|---|---|---|---|
| 4023414 | 2/1991 | Germany . | |
| 0067552 | 3/1988 | Japan | 378/57 |

Primary Examiner—David P. Porta
Attorney, Agent, or Firm—Spencer, Frank & Schneider

[57] ABSTRACT

A simplified and improved object testing system which, according to the present invention, includes a first and a second imaging system for generating a radiograph of the object as a visible image on a monitor, and a common operating unit controlling the first and second imaging system.

19 Claims, 2 Drawing Sheets

OBJECT TESTING SYSTEM

This is a continuation application of application Ser. No. 08/094,387 filed Jul. 20, 1993.

BACKGROUND OF THE INVENTION

1. Technical Field of the Invention

The present invention is directed to an apparatus for inspecting articles using a radiation beam, and in particular, to an apparatus for inspecting articles using a radiation beam utilizing a controller for controlling and manipulating a plurality of images produced by the apparatus.

2. Background Art

DE-4,023,414.A1 to Bermbach et al. discloses a device for irradiating objects with fan-shaped radiation used scan the contents of objects, for example, in airports for detecting bombs, weapons and smuggled goods. The device includes a first imaging system and a second imaging system, where each imaging system includes a radiation emitter and an associated radiation receiver. According to Bermbach et al., it is possible to irradiate an object from different directions. Signals corresponding to radiograph signals received by the radiation receivers are directed to an image processing device including a computer for creating a visible image on a monitor of the imaging system from the received signals.

Each imaging system of the Bermbach et al. system includes an operating unit for presetting recording parameters required for each image for the radiation emitter and manipulating visible images.

SUMMARY OF THE INVENTION

The present invention provides an object testing system with simplified and improved operation over the prior art. The above and other objects of the invention are accomplished by the provision of an object testing system including a first imaging system for generating a first image on a first monitor from a first radiograph of the object, a second imaging system for generating a second image on a second monitor from a second radiograph of the object, and a common operating unit coupled to the first and the second imaging systems for controlling the generation of the first and the second images.

An advantage of the present invention is that only a single common operating unit is provided for controlling the first and the second imaging systems, simplifying operation of the imaging systems. Operation is simplified if the imaging systems are individually or jointly controllable from the common operating unit. Thus, the object testing system according to the present invention can be operated more economically since a second operating unit is no longer necessary.

Preferably, signals from the common operating unit are applied to the first and/or second imaging system by way of a signal distributor. The signal distributor directs signals from the common operating unit either to the first and/or to the second imaging system.

As a further advantageous feature, it is possible to control the present invention with the common operating unit so that the first or the second imaging system operates as a master system or, in the alternative, a slave system. Consequently, the two imaging systems are able to communicate with one another. In particular, data and signals are transmitted from one imaging system to the other imaging system.

As a particularly advantageous feature, it is possible to display a first view of the object on the monitor of the first imaging system and a second view of the object on the monitor of the second imaging system, while simultaneously manipulating the two displays by the common operating unit. Separate manipulation of the respective displays is no longer required for each imaging system. This feature is particularly advantageous for simultaneously displacing the displays on the respective monitors using the common operating unit. It is thus possible to display a plan view of the object on the monitor of the first imaging system and a side view of the object on the monitor of the second imaging system, and shift the displays in synchronism relative to one another on the respective monitor screens.

According to another aspect, the present invention further includes a distributor, coupled between the common operating unit and the first imaging system and between the common operating unit and the second imaging system, for coupling signals output by the common operating unit to the first and second imaging systems. The common operating unit also controls signal coupling between the first and second imaging systems.

According to yet another aspect of the present invention, a first image of a first view of the object is displayed on a first monitor and a second image of a second view of the object is displayed on a second monitor, such that the first image and the second image are simultaneously manipulated by the common operating unit. That is, the common operating unit can provide simultaneous shifting of the displays on the first and second monitors.

According to still another aspect of the present invention, the common operating unit controls at least one window displayable on one of the monitors for evaluating an image displayed on the screen of at least one monitor, in addition to controlling the first and second imaging systems to display a first and a second view of an object on the first monitor.

According to a further aspect of the present invention, there is provided an object testing system for producing images of an object including a first imaging system including a first processor, a first radiation transmitter coupled to the first processor for transmitting radiation at the object, a first radiation receiver for receiving a first radiograph of the object from radiation transmitted from the first radiation transmitter and producing a first signal representing the first radiograph, the first processor responsive to the first signal for producing an image on a first monitor from the first signal, a second imaging system including a second processor, a second radiation transmitter coupled to the second processor for transmitting radiation at the object, a second radiation receiver for receiving a second radiograph of the object from radiation transmitted from the second radiation transmitter and producing a second signal representing the second radiograph, the second processor responsive to the second signal for producing an image on a second monitor from the second signal, and a common controller coupled to the first and second imaging systems for controlling operation of the respective imaging systems and for manipulating images produced on the respective monitors.

According to still another aspect, the present invention further includes a signal distributor, coupled between the first imaging system and the common controller and coupled between the second imaging system and the common controller, and controlled by the common controller for directing signals output from the common controller to at least one of the imaging systems. Accordingly, the common controller controls the signal distributor for configuring signal coupling between the first and second imaging systems, and can configure the first imaging system as a master imaging system and the second imaging system as a slave imaging system under control of the master imaging system. Images produced on the respective monitors are simultaneously manipulated by the common controller. For example, the common controller can control the first and second imaging systems to display two images on at least one monitor, or control the first and second imaging systems and the signal distributor to display two images on at least one monitor. The common controller can, for example, also manipulate an image produced by an imaging system by changing colors displayed or manipulate images produced by the first and second imaging systems by simultaneously shifting the respective images.

Further advantages and details of the invention will become evident from the following description with reference to the drawing of one embodiment of the object testing system according to the present invention.

DETAILED DESCRIPTION OF THE PREFERRED EMBODIMENT

Figure 1:
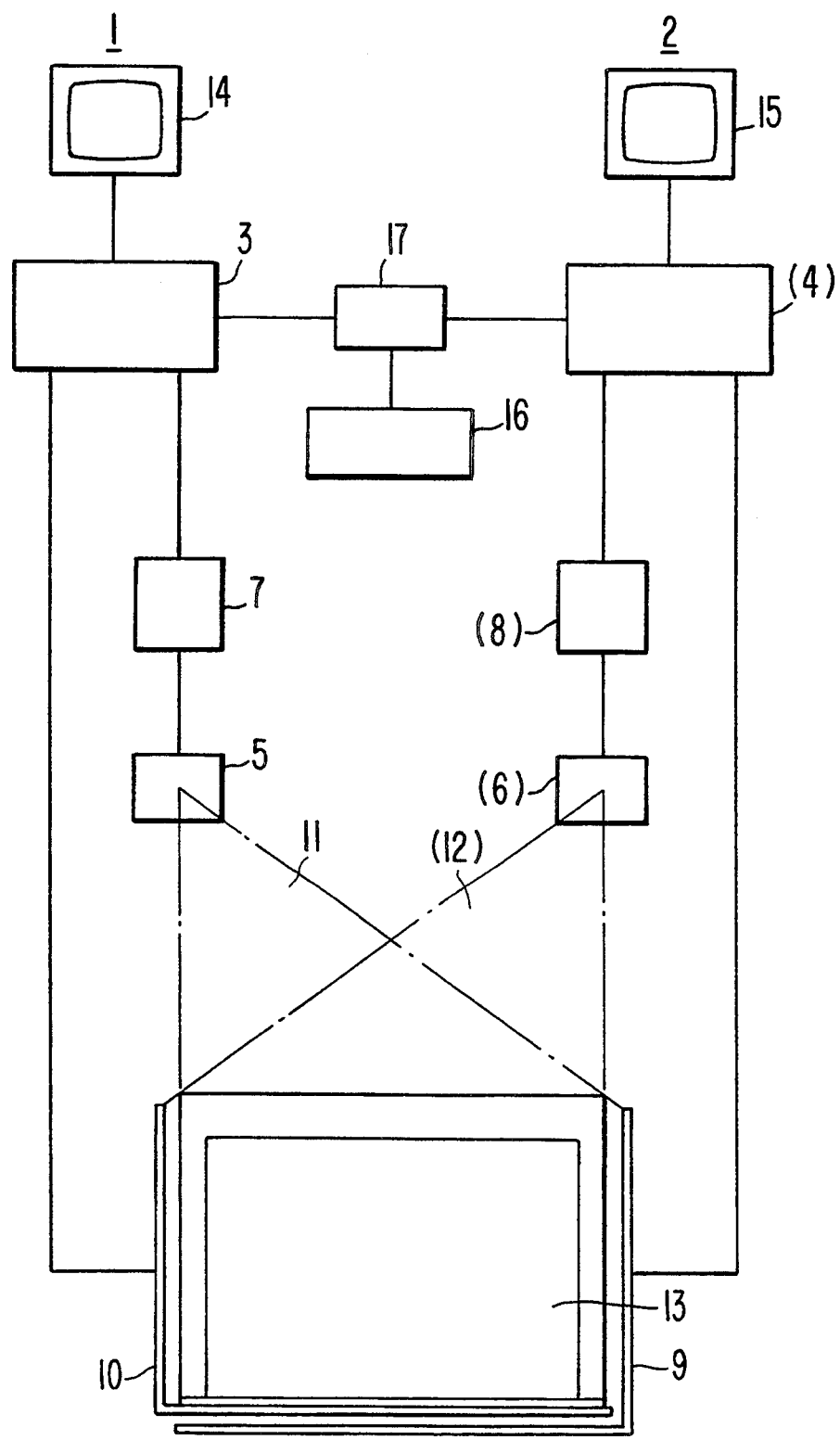
FIG. 1 is a schematic block diagram of one embodiment of a testing system for objects according to the present invention.

FIG. 1 is a schematic block diagram showing a testing system, according to the present invention, for objects such as freight, vessels, containers and/or vehicles. The system includes a first imaging system 1 and a second imaging system 2. Imaging systems 1 and 2 include the same functional elements, consequently, various functional elements of the second imaging system 2 are identified, at times, by bracketed reference numerals. As shown, imaging system 1 (2) includes, for example, a processing unit 3 (4) for controlling recording unit equipped with a radiation transmitter 5 (6) which is supplied with energy by generator 7 (8). Radiation transmitter 5 (6) has an associated radiation receiver 9 (10) for receiving radiation beam 11 (12) transmitted from radiation transmitter 5 (6) after beam 11 (12) has penetrated an object under test, for example, container 13, as a radiograph of container 13. Radiation receiver 9 (10) converts the received radiograph into electrical signals which are output to processing unit 3 (4). In response, processing unit 3 (4) generates a visible image of radiation receiver 9 (10) from the output signals on monitor 14 (15). To improve detection of objects in container 13, container 13 is preferably irradiated from different directions by radiation emitters 5 and 6 so that different views of container 13 appear as displays on monitors 14 and 15.

The object testing system of FIG. 1 can include more than two imaging systems for producing a plurality of images for testing objects. Moreover, the object testing system according to the present invention can be coupled to a host computer for access to a data base or other data processing.

The object testing system of the present invention further includes a common operating unit 16 whose signals are coupled to processing units 3 and 4. Common operating unit 16 can be a microprocessor connected to associated peripheral components, such as random access memory (RAM), read only memory (ROM), a mass storage device such as disk drive, and communication components, or can be dedicated logic circuits, such as programmed logic devices, or discrete components. Processing units 3 and 4 can also be formed from a similar microprocessor system, or from dedicated logic circuits or discrete components.

Recording parameters of radiation transmitter 5 and 6, configured, for example, as an X-ray tube (KV, mA, t), can be set separately or jointly by common operating unit 16 for each recording system of the present invention through a keyboard (not shown). In addition, the displays on monitors 14 and 15 can be simultaneously manipulated. For example, the contrast and/or brightness of the displays can be changed. Preferably, however, common operating unit 16 is used to simultaneously shift or change the displays of container 13 on monitors 14 and 15 so that, for example, a side view and a top view of container 13 are shifted or changed in synchronism.

Signal distributor 17 is connected between common operating unit 16 and processing units 3 and 4 for coupling the signals output from common operating unit 16 to processing unit 3 and/or to processing unit 4. Signal processor 17 can be a bank of automatically controlled multiplexers, semiconductor switches, transistors, relays or manually controlled toggle switches. The multiplexing function may also be accomplished by a computer system. It is thus possible to apply data and other signals output from common operating unit 16, for example, to processor unit 3 for processing. The processed signals may then be coupled through signal distributor 17 to processing unit 4 for controlling the second imaging system 2. In this situation, processing unit 3 is a master imaging system processor and processing unit 4 a slave imaging system processor. Of course, it is within the scope of the present invention for processing unit 4 to operate as a master imaging system processor and processing unit 3 operate as a slave imaging system processor.

Function elements in common operating unit 16 operate for determining whether output signals from common operating unit 16 coupled to processing unit 3 or 4 are also coupled processing unit 4 so that processing operations and display manipulations are performed individually or jointly by processing units 3 and 4. Master imaging system processor the processing unit where the image is manipulated directly via common control unit 16. On the slave imaging system processor the image is automatically changed also (according to the degree of coupling and the selection of commonly controlled functions chosen).

For example, particular colors may be assigned to particular gray values associated with radiation absorption. Through operation of common operating unit 16, the present invention can be configured so that both displays of monitors 14 and 15 are in color or one display is in gray values and the other display is in color. The displays may also be shifted, or changed, individually or in synchronism on the respective screens of monitors 14 and 15. Common operating unit 16 can also configure whether, for example, contrast and/or brightness of the respective displays are changed individually or jointly in a similar or a different manner. Additional examples of possible common operations are the parallel start of image generation, the parallel load or storage of images or the configuration of system parameters. Thus, common operating unit 16 can configure the degree of simultaneous manipulation and coupling between the master and slave imaging system.

If the object testing system according to the present invention is equipped with two monitors 14 and 15, synchronized video signals can be provided to the monitors by the present invention in order to avoid interference and flicker phenomena on their respective screens. It is also possible, according to the present invention, to display a plan view and a side view of the object, for example, on the screen of one monitor which is manipulated by common operating unit 16.

Figure 2:
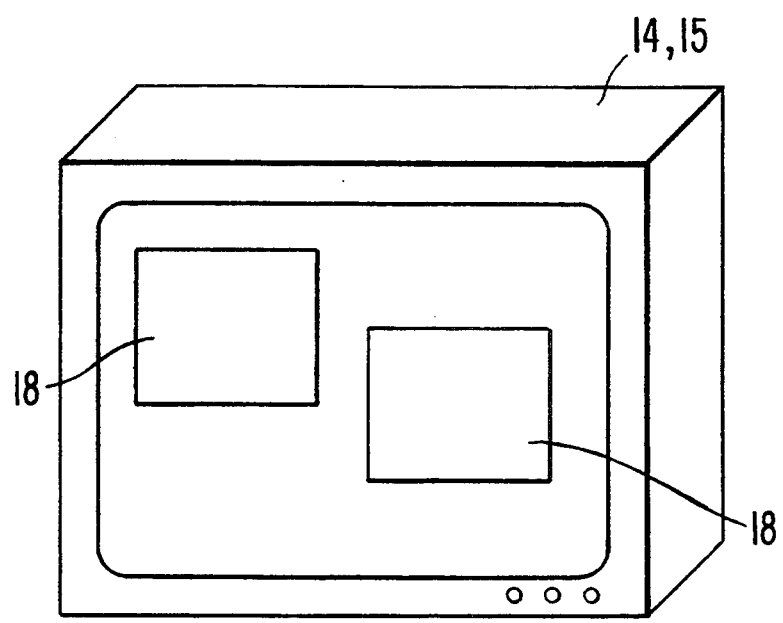
FIG. 2 shows an example of the presentation of two views on a single monitor using so-called windows.

As a further feature of the object testing system according to the invention, the system generates a window for evaluating the display on the screen of one monitor or screens of both monitors 14 and 15, with the window(s) being controllable by common operating unit 16. Of course, several windows may also be controlled to evaluate a particular display on the monitor screen. This is shown in FIG. 2 for clarity. As is known, computer workstations and personal computers often offer a graphical user interface where several windows on the monitor may ease the work of the computer user. With simple operations, a user can activate the momentarily interesting window and switch between windows for quasi-simultaneous work.

For use with the object testing system according to the invention, e.g., two views of the object are generated by the system and may be displayed in two windows (18, 19) on a single monitor (14, 15). The common operating unit 16 then controls the images in those windows in the same way as described in the two monitor case. The second monitor must not be available when using windows. But there are applications where the use of more than one monitor has additional advantages.

To simplify operation, input to common operating unit 16 for configuring recording parameters, controlling the imaging systems and manipulating displays, may be accomplished not only by a keyboard, but also, for example, by a mouse, a joystick, a trackball or any desired combination of these, or other, input devices.

Additional modifications and changes may be made to the disclosed embodiment of the present invention, however, the invention is not limited to the specific details set forth. Accordingly, modification may be made without departing from the spirit or scope of the concept of the present invention as defined by the appended claims and their equivalents.

What is claimed is:

1. An object testing system, comprising:
   a first imaging system for generating a first image on a first monitor from a first radiograph of an object;
   a second imaging system for generating a second image on a second monitor from a second radiograph of the object; and
   common operating means coupled to the first and the second imaging systems for controlling the generation of the first and the second images, and for controlling whether the first or the second imaging system operates as a master imaging system or a slave imaging system.

2. An object testing system according to claim 1, wherein the first and second imaging systems are individually or jointly controlled by the common operating means.

3. An object testing system according to claim 1, further comprising a distributor, coupled between the common operating means and the first imaging system and between the common operating means and the second imaging system, for coupling signals output by the common operating means to the first and second imaging systems.

4. An object testing system according to claim 1, wherein the first imaging system is controlled to display a first and a second view of the object on the first monitor.

5. An object testing system according to claim 4, wherein the common operating means controls at least one window displayable on one of the monitors for evaluating at least one image displayed on the screen of at least one monitor.

6. An object testing system according to claim 1, wherein a first image of a first view of the object is displayed on the first monitor and a second image of a second view of the object is displayed on the second monitor, and wherein the first image and the second image are simultaneously manipulated by the common operating means.

7. An object testing system according to claim 1, wherein the common operating means provides simultaneous shifting of the displays on the first and second monitors.

8. An object testing system according to claim 6, wherein signal coupling between the first and second imaging systems are controlled by common operating means.

9. An object testing system according to claim 1, wherein the common operating means controls at least one window displayable on one of the monitors for evaluating an image displayed on the screen of at least one monitor.

10. An object testing system for producing images of an object, comprising:
   a first imaging system including a first processor, a first radiation transmitter coupled to the first processor for transmitting radiation at the object, a first radiation receiver for receiving a first radiograph of the object from radiation transmitted from the first radiation transmitter and producing a first signal representing the first radiograph, the first processor responsive to the first signal for producing an image on a first monitor from the first signal;
   a second imaging system including a second processor, a second radiation transmitter coupled to the second processor for transmitting radiation at the object, a second radiation receiver for receiving a second radiograph of the object from radiation transmitted from the second radiation transmitter and producing a second signal representing the second radiograph, the second processor responsive to the second signal for producing an image on a second monitor from the second signal; and
   a common controller coupled to the first and second imaging systems for controlling operation of the respective imaging systems, for manipulating images produced on the respective monitors and for configuring the first imaging system as a master imaging system and the second imaging system as a slave imaging system under control of the master imaging system.

11. An object testing system according to claim 10, further comprising a signal distributor, coupled between the first imaging system and the common controller and coupled between the second imaging system and the common controller, and controlled by the common controller for directing signals output from the common controller to at least one of the imaging systems.

12. An object testing system according to claim 11, wherein the common controller controls the signal distributor for configuring signal coupling between the first and second imaging systems.

13. An object testing system according to claim 10, wherein images produced on the respective monitors are simultaneously manipulated by the common controller.

14. An object testing system according to claim 10, wherein the common controller controls the first and second imaging systems to display two images on at least one monitor.

15. An object testing system according to claim 11, wherein the common controller controls the first and second imaging systems and the signal distributor to display two images on at least one monitor.

16. An object testing system according to claim 10, wherein the common controller controls at least one of the imaging systems to generate at least one window displayable on one of the monitors for evaluating at least one image displayed on the screen of at least one monitor.

17. An object testing system according to claim 11, wherein the common controller controls at least one of the imaging systems to generate at least one window displayable on one of the monitors for evaluating at least one image displayed on the screen of at least one monitor.

18. An object testing system according to claim 10, wherein the common controller manipulates an image produced by an imaging system by changing colors displayed.

19. An object testing system according to claim 10, wherein the common controller manipulates images produced by the first and second imaging systems by simultaneously shifting the respective images.

* * * * *